(12) United States Patent
Diduch et al.

(10) Patent No.: US 8,400,880 B2
(45) Date of Patent: Mar. 19, 2013

(54) DISPLAY FOR USE IN MANAGING MOVEMENT OF A PATIENT IN A BED

(75) Inventors: Robin Diduch, Winnipeg (CA); Matthew Peter Braun, Niverville (CA)

(73) Assignee: Safe Moves Injury Prevention Solutions Inc, Winnipeg, MB (CA)

( * ) Notice: Subject to any disclaimer, the term of this patent is extended or adjusted under 35 U.S.C. 154(b) by 415 days.

(21) Appl. No.: 12/876,628

(22) Filed: Sep. 7, 2010

(65) Prior Publication Data
US 2012/0057433 A1    Mar. 8, 2012

(51) Int. Cl.
*G04B 47/00* (2006.01)
*G04B 45/00* (2006.01)
*G04B 19/00* (2006.01)
*G09F 9/00* (2006.01)

(52) U.S. Cl. ............. 368/10; 368/41; 368/223; 116/308

(58) Field of Classification Search .................... 368/10, 368/41, 80, 223; 116/308; 283/2, 3, 115, 283/900
See application file for complete search history.

(56) References Cited

U.S. PATENT DOCUMENTS

| | | | | |
|---|---|---|---|---|
| 5,583,832 | A * | 12/1996 | DePonty | 368/10 |
| 6,014,346 | A * | 1/2000 | Malone | 368/10 |
| 6,031,791 | A | 2/2000 | Thoni | |
| 7,027,358 | B1 * | 4/2006 | Esposito et al. | 368/10 |
| 2009/0016168 | A1 * | 1/2009 | Smith | 368/10 |

* cited by examiner

*Primary Examiner* — Vit W Miska
(74) *Attorney, Agent, or Firm* — Adrian P. Battison; Ade & Company Inc

(57) ABSTRACT

A system is provided for communicating to health care workers the turning, positioning and schedule requirements of dependent patients with pressure ulcers, or at risk for the development of pressure ulcers. The system includes a display indicating a next required position of the patient and a display indicating a time for next movement of the patient to the next position. The time of next movement is calculated by entering an indication of a maximum allowable time for the patient to remain in each position and adding this to the current time.

20 Claims, 5 Drawing Sheets

DISPLAY FOR USE IN MANAGING MOVEMENT OF A PATIENT IN A BED

This invention relates to a display apparatus for use in managing movement of a patient in a bed between different positions of lying.

BACKGROUND OF THE INVENTION

Pressure wounds are costly in regards to human suffering and human resource utilization across healthcare settings. In the United States, reported incidence or pressure ulcers and wound care in acute settings range from 2% to 29% and costs have been reported from $2000 to $70,000 per wound (Arnold, 2003). It is estimated that 2.5 million clients are treated every year for wounds related to pressure, of which 60,000 die from complications.

According to the Canadian Association of Wound Care (CWAC) there are 12 recommendations to manage and prevent pressure ulcers. One of these recommendations looks at the importance of assessing and modifying the client's environment, which focuses on the importance of turning and positioning the client in bed to offload pressure and prevent ulcers.

Being able to position clients to relieve pressure is a fundamental skill in health care that requires the practical ability that is vital to enhancing a client's physical, social, and psychological wellbeing. Correct therapeutic positioning of clients is essential to maximize physiological functioning and recovery. Poor bed positioning can compromise a client's airway, cause joint dislocations, displacement of fractures, peripheral nerve damage, spasms and pressure ulcers.

The recommendations for positioning focus on treating pressure ulcers, however, the principles can be applied to other types of wounds that require pressure relief. The positions and principles can be generalized to suit the client's individual needs. Frequent turning and proper re-positioning will help decrease the pressure forces and reduce the chance of wounds related to pressure from occurring. To accomplish this it is important to educate health care workers and the client on proper positioning techniques to enhance the client's physical and psychological wellbeing. Thus interrupted or reduced pressure on wounds will reduce ischemia and will likely improve tissue healing. However only full body change of position completely relieves pressure.

According to best practice, clients should be repositioned at least every 2 hours. However, the turning and positioning schedule should be individualized to the client's needs, which depends on the type and severity of the wound.

It has been proposed to use diagrams with clocks and body positions of clients are helpful in reminding health care workers when and how to position the client. Turning schedules featuring crude pictures of clocks or sign off sheets are commonly used in healthcare settings but lack the required functionality in regards to the ability to substantially individualize the routine, provide a clear picture as to how the client should be positioned, and allow ease of supervision of the routine.

SUMMARY OF THE INVENTION

It is one object of the invention to provide a display apparatus for use in managing movement of a patient in a bed.

According to one aspect of the invention there is provided a display apparatus for use in managing movement of a patient in a bed between a plurality of separate positions of lying in the bed, comprising:

a substrate for supporting elements to be displayed;

a plurality of first display elements each providing an indication of a required position for the patient;

the substrate providing a plurality of locations each for receiving a respective one of the first display elements;

a second display element arranged to provide a display associated with a respective one of the locations for indicating a current position of the patient;

a third display element arranged to provide a display indicating a next required position of the patient;

a fourth display element arranged to provide a display indicating a time for next movement of the patient to the next position.

Preferably there is provided an input for entering an indication of a maximum allowable time for the patient to remain in each position.

Preferably the fourth display element is arranged to display the time for next movement based on a calculation of adding the maximum allowable time to the current time.

This can be done manually by entering the time on the substrate and by the care provider doing a simple calculation. In an electronic version, there is provided control unit which receives the input of the maximum allowable time and automatically adds this to a clock signal indicating the current time.

In a manual version the clock is manually moved to the required time display. In the electronic version using an electronic clock display, the fourth display element is arranged to display the actual time for the next movement and a time period to elapse before the next movement.

Preferably there are six locations and with three or two separate positions.

Preferably the locations are arranged sequentially around a center of the substrate.

Preferably the fourth or time display element is located in the center of the locations.

Preferably the first display elements each include a graphic symbol indicative of the respective position of the patient.

Preferably the fourth or time display comprises a graphic symbol of a clock.

Preferably the fourth or time display is set manually.

Preferably there is provided a further display element which indicates the requirement of the patient to be removed from the bed for meals.

Preferably there is provided a further display element which indicates the requirement of the patient to be removed from the bed for placement in a chair.

Preferably the substrate is arranged for removably receiving the first display elements for selective positioning in the locations.

Preferably the substrate is a magnetic board with a surface which can be marked and erased and the first display elements are magnetic for selective positioning in the locations or can be of other removable constructions.

In the manual version the second display element of the current position is arranged to be moved manually to a selected one of the locations.

In the electronic version the second display element comprises a plurality of illuminated buttons each associated with a respective location and each operable to indicate a selected one of the locations.

According to a second aspect of the invention there is method for managing movement of a patient in a bed between a plurality of separate positions of lying in the bed, comprising:

providing a plurality of first display elements each providing an indication of a required position for the patient;

causing a health care provider to enter an indication of a current position of the patient;

providing a display indicating a next required position of the patient;

entering an indication of a maximum allowable time for the patient to remain in each position;

and providing a display indicating a time for next movement of the patient to the next position.

BRIEF DESCRIPTION OF THE DRAWINGS

One embodiment of the invention will now be described in conjunction with the accompanying drawings in which.

In the drawings like characters of reference indicate corresponding parts in the different figures.

DETAILED DESCRIPTION

Figure 1:
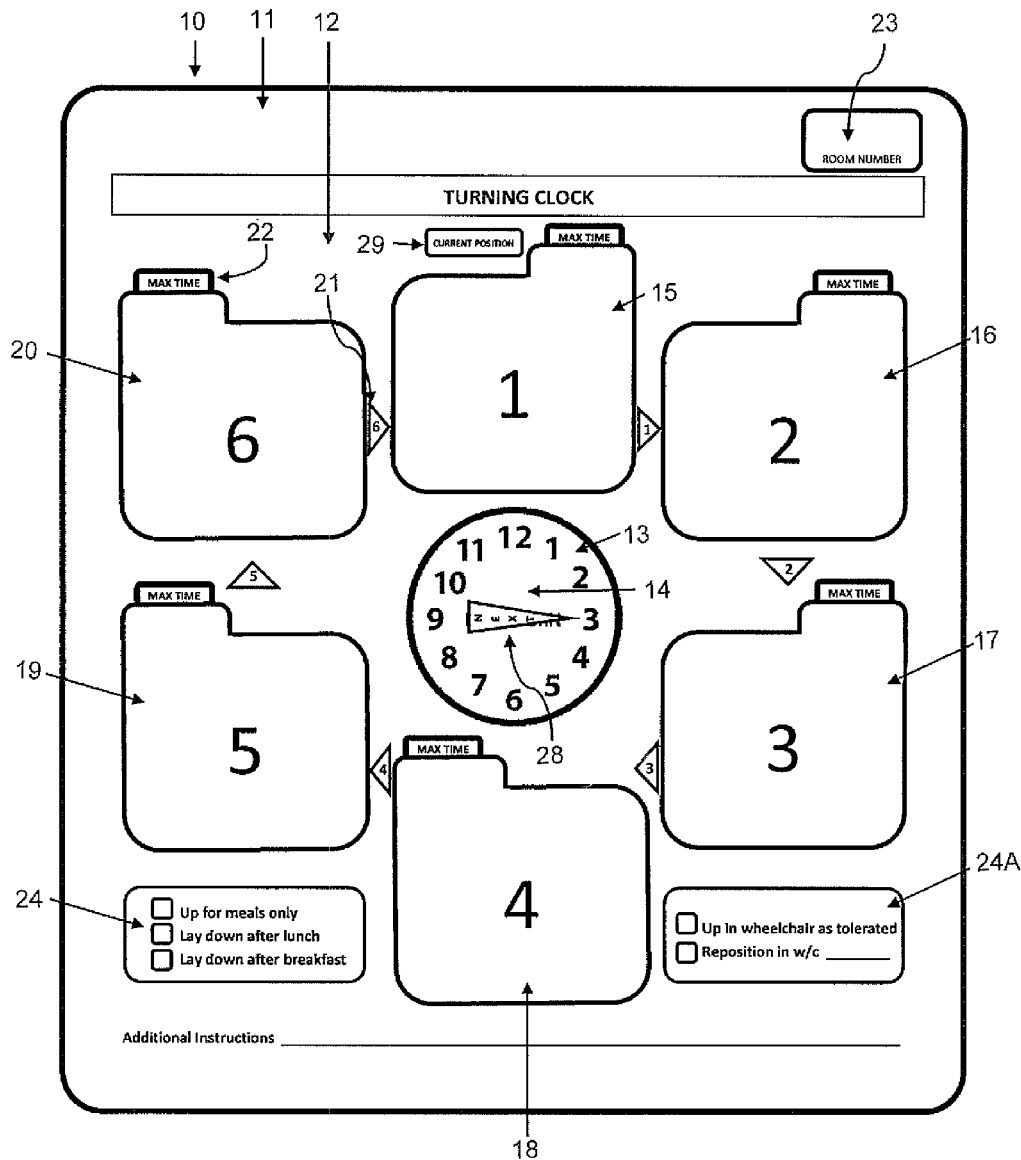
FIG. 1 is a front elevational view of a first manual version of an apparatus according to the present invention.
Figure 2A:
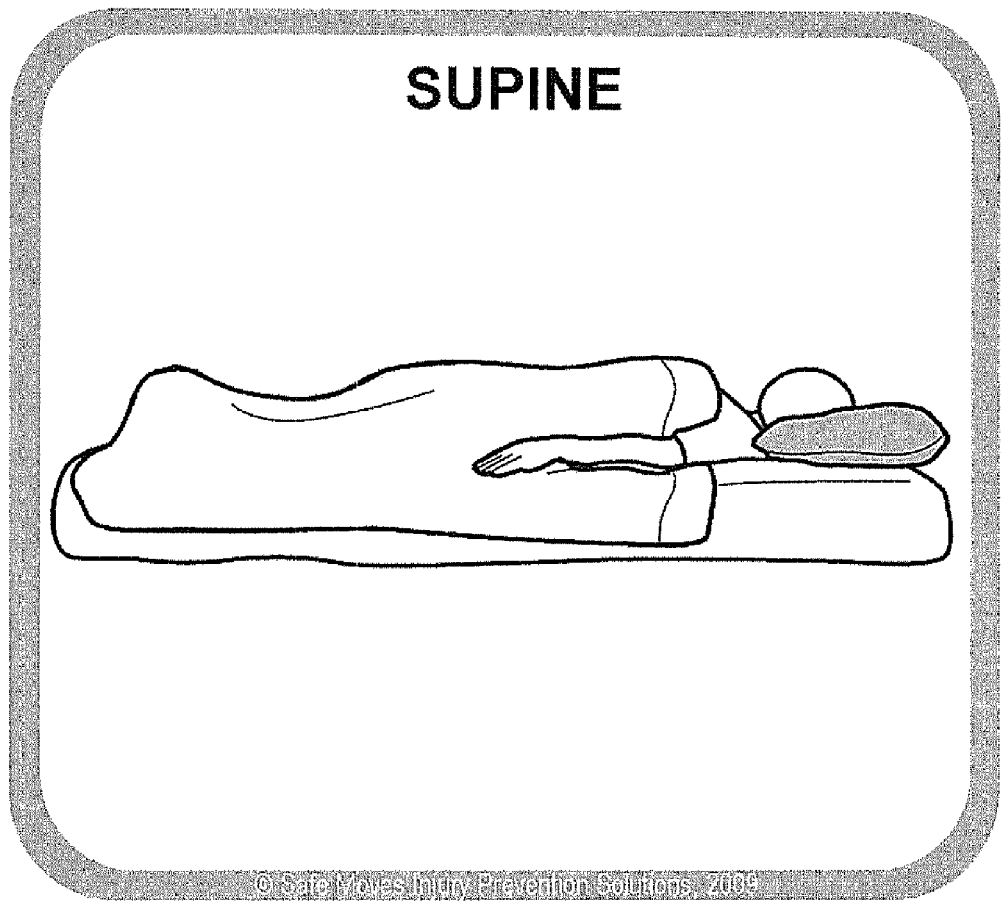
FIGS. 2A to 2C are plan views of separate panels which display different positions to be taken up by the patient.
Figure 2B:
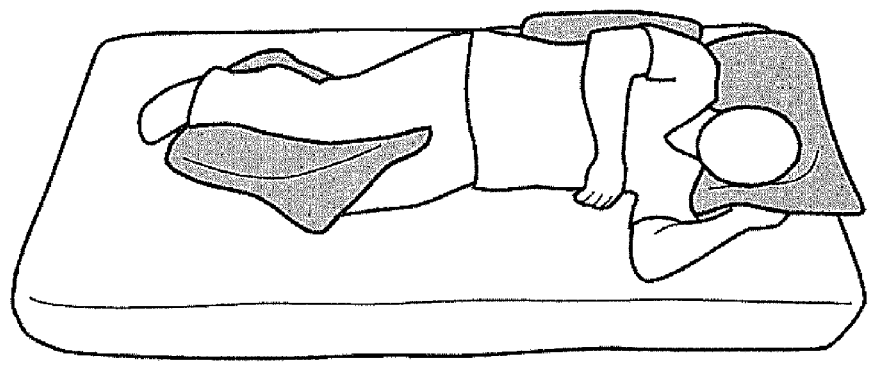
Figure 2C:
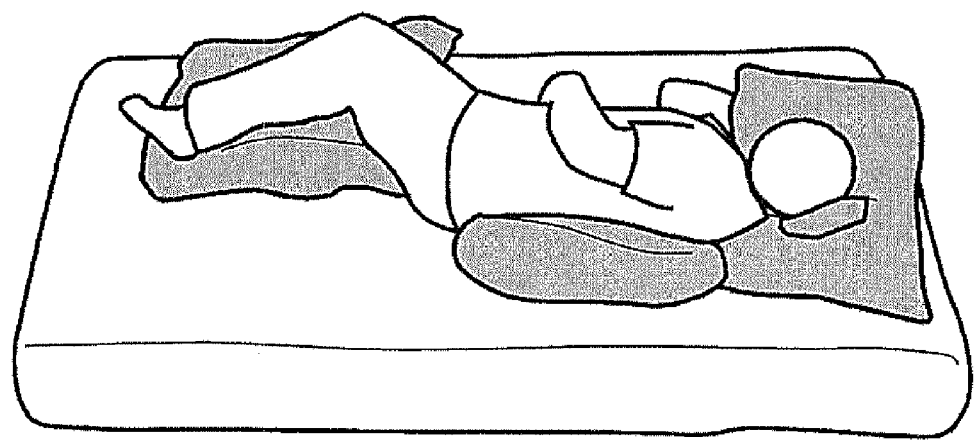

A first embodiment is shown in FIG. 1 and comprises a flat rectangular board 10 arranged to be located on a wall or adjacent the bed of a patient. The board has a front face 11 with a coating 12 of a known characteristic which is arranged to form a wet/dry erase board for marking with desired graphics or words and includes a ferromagnetic layer for attachment thereto of one or more magnetic logos. The front face of the board carries printing graphics on it as shown in FIG. 1.

A first item of the graphics located in a center of the board is indicated at 13 and comprises an image 14 of a clock face with conventional numbered hours around the periphery. The graphics include six boxes numbered 1 to 6 and indicated at 15 to 20 surrounding the clock. The graphics include a plurality of arrows 21 which are located between each box and the next indicating a clockwise direction from one box to the next with the arrows also numbered 1 to 6. The graphics further include a plurality of tabs 22 each of which is provided on the top of a respective box with the label "Max Time" and a space of sufficient size to write in manually a time limit in hours.

The graphics further include a box 23 in the upper right hand corner which includes a designation of the client's room number with an open space allowing the information to be added manually on the wet/dry erase material of the board.

The graphics further include a box 24 in the lower left of the board is utilized to indicate when or whether the client can be removed from the bed to a seating position for meals. That is the graphics provide a series of options relating to the ability of the patient to be removed from the lying position and boxes allowing a check mark to be applied indicative of the option selected, dependent on the abilities and condition of the patient.

The graphics further include a box 24A in the lower right of the board indicates how often to remove the patient from the bed for repositioning the patient in wheelchair. That is the graphics provide a series of options relating to the ability of the patient to be removed from bed to a wheelchair and boxes allowing a check mark to be applied indicative of the option selected, dependent on the abilities and condition of the patient.

The very bottom of the board includes graphics which allow a space for writing in any additional instructions the health care provider needs to be aware of.

All writing on the board is done utilizing a dry or wet erase pen.

Working in combination with the board are five different magnetic panels each with art work printed on it that are utilized to indicate the turning and positioning requirements of the client. The magnetic panels, as shown in FIG. 1 and FIGS. 2A to 2C, include:

A panel 25 indicating the position "Supine" (FIG. 2A) with printed artwork showing a client lying on their back in a supine position.

A panel 26 indicating the position "Right Partial Side Lying" (FIG. 2B) with printed artwork showing a client positioned in right partial side lying.

A panel 27 indicating the position "Left Partial Side Lying" (FIG. 2C) with printed artwork showing a client positioned in left partial side lying.

The above three panels 25, 26 and 27 are shaped and arranged to sit over respective ones of the boxes 15 to 20 without the panel impinging on another of the boxes or the clock 14 or other box of the board.

The three panels indicate all of the separate positions that are suitable for a patient in this condition. The number of boxes, which is selected as six, allows only a situation where only two of the positions to be selected or all three of the positions to be used. Thus when two positions only are used, each of the six boxes will be filled with alternate ones of the two positions to be used, thus requiring three sets of two panels of each position. Where all three positions are to be used for the patient, two sets of three panels are used and are placed consecutively in the six boxes.

A panel 28 indicating a small arrow utilized to mount on the center area of the clock to indicate the time of the next turn on the center clock and movable by magnetic connection for repositioning to identify the next position to be used for the positioning of the patient.

A panel 29 indicating "Current Position" which is a small magnetic panel that is place beside the selected one of the panels 25, 26 or 27 in the selected one of the boxes 15 to 20 to indicate how the client should currently be positioned in bed.

To utilize the clock the magnetic panels 25, 26 or 27 with artwork are arranged in each of the boxes arranged in a clockwise pattern around the board according to the individual needs of the client. For example a client with a coccyx ulcer would typically not be placed in supine and would not utilize the supine logo so that the boxes 15 to 20 would contain alternate ones of the panels 26 and 27. Thus the right and left partial side lying panels would be alternated in the 6 clockwise boxes around the board indicating the client is to be turned between these two positions. Based on their clinical reasoning the health care provider is required to indicate in the max time tab 22 the amount of time the client should spend in that position before being turned again, for example 1 hour or 2 hours.

The health care provider is required to indicate in box 23 the room number or bed number for the client. The health care provider is required to indicate in box 24 how often the client should be out of bed. The health care provider is required to indicate in box 24A how often the client should be repositioned in their wheelchair.

The Current Position magnet panel 29 is placed on the board, adjacent to the box 15 to 10 displaying the current position, by the health care worker to indicate the position the client is currently in. The Next magnet panel 28 is placed on the board within the clock to indicate the time the health care worker needs to return to complete the next turn of the client. The time of the next turn is calculated by adding the time within the max time tab of the box 15 to 20 to the current time.

For example if the current time is noon and the max time tab beside the current position magnet indicates 2 hours, the Next magnet would be positioned to point to the 2 printed within the clock. At the time of the next turn the health care worker should return, reposition the client according to the magnet clockwise to the next box and move the current position magnet panel clockwise above this magnet panel in the box concerned. The Next magnet 28 is then be moved again to indicate the time of the next turn as indicated by the max position tab 22. This process continues following the magnet panels clockwise around the board as long as the client remains in bed.

Figure 3:
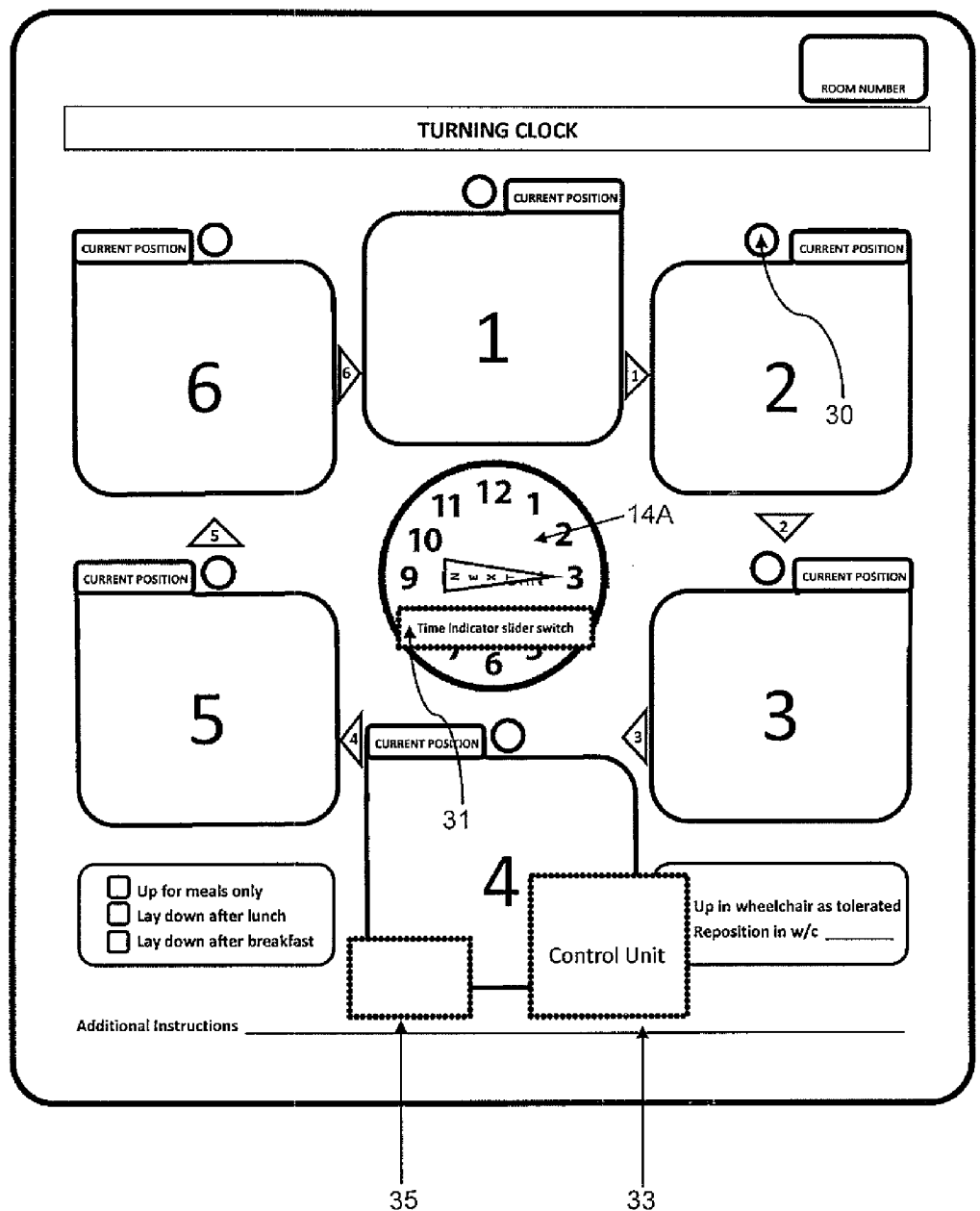
FIG. 3 is a front elevational view of a second electronic version of an apparatus according to the present invention.

Turning now to FIG. 3 there is shown an electronic version of the arrangement described above. This comprises a board and magnetic panels substantially as previously described.

In this embodiment the board is modified to comprise an electric board with built in timer and indicator lights. Thus the board now includes a control unit 33 which operates the time on the electronic clock 14A which is activated in response to inputs from a current position illuminated button 30 and from a timer input 31.

Thus instead of using markers and panels 14 and 29, the board has indicator lights carrying out these functions. The electronics of the board are powered by a battery or AC adapter. This clock is a numbered digital LED clock in the center and is illuminated to a low level at all times. The on/off switch 35 for the board is located on the back of the board. There are as described previously 6 boxes 15 to 20 surrounding the clock 14 with an arrow 21 between each box indicating a clockwise direction.

Above each of the boxes 15 to 20 is a "Current Positioning" indicator light in the form of a press button 30 that lights up when activated. On the clock is provided a timer input 31 which is used to set the amount of time for which the patient should remain in the current position.

As previously, a box in the upper right hand corner of the board indicates the client's room number. A box in the lower left of the board is utilized to indicate when the client can be up. A box in the lower right of the board indicates how often to reposition in wheelchair. The very bottom of the board allows space for writing in any additional instructions the health care provider needs to be aware of. All writing on the board is done utilizing a dry or wet erase pen.

To utilize the clock the selected magnetic panels with artwork are placed in each of the boxes arranged in a clockwise pattern around the board according to the individual needs of the client. The selected current Position illuminated indicator button 30 is pushed by the health care provider to indicate the position the client is currently in and illuminates when activated. The digital LED clock then is operated to indicate the time the health care provider needs to return to complete the next positioning change of the client. This can be set at one, one and a half or two hours after the time the current position button is activated. The length of time is selected by utilizing the slider switch 31 on the LED clock to select between one hour, one and a half hours and two hours.

After the Current Position button is activated the LED clock will alternate between flashing the actual time of the next turn and displaying the time remaining until the next turn. At the time of the next turn the health care provider will be notified by flashing the activated current position light.

Variations can include:
Activating an audible buzzer utilizing a built in speaker.
Activating a nurse call bell system through a wired interface.
Activating a nurse call bell system through a non wired interface (wifi, radio signal, Bluetooth etc.)
Sending a text message to a hand held PDA, cell phone, or computer
Activating a wireless pager At the time of the next turn, the health care provider is caused to return, reposition the Client according to the next position panel in the clockwise progression of the boxes 15 to 20 and then is required to press the new "Current Position" button above the next box. At this point, the control system 33 acts to control the lights and the clock so that the light is automatically turned off on the previously activated "Current Position" button and the newly activated "Current Position" button lights up. Simultaneously, the digital clock automatically indicates the time of next position change. This process continues following the magnet panels in the boxes 15 to 20 clockwise around the board as long as the client remains in bed.

If the healthcare provider does not reposition the Client within the set time limit, both the digital clock and the "Current Position" indicator button will begin to blink once the limit is exceeded. This blinking indicates to both supervisors and other workers that the time limit has been exceeded. However, once the health care provider changes the Client's position and presses the "Current Position" button above the next box in the progression, the blinking stops as the clock sets forward by the required set time to indicate the time of next position change. As before, the "Current Position" indicator button lights up to indicate the position in which the Client is currently in.

In accordance with another version (not shown), a software based program can be provided that incorporates the concepts of version 2 and version 1 but does not utilize a physical board in the client's room. Turning schedule for the client is set up in the software program on a computer, PDA, or cell phone. At the time of each reposition a message is sent wirelessly through the internet or utilizing a text message system to the health care provider's cell phone, PDA, wireless pager or computer indicating it is time to reposition the client. On internet based versions a picture of the position to turn the client into will be displayed and the healthcare provider will send a signal back to the main computer via their hand held device to indicate they have received the message and the turn has been completed. On text message version the position to turn the client into will be described in text. The cycle will continue as long as the Client is in bed.

Since various modifications can be made in my invention as herein above described, and many apparently widely different embodiments of same made within the spirit and scope of the claims without department from such spirit and scope, it is intended that all matter contained in the accompanying specification shall be interpreted as illustrative only and not in a limiting sense.

The invention claimed is:

1. A display apparatus for use in managing movement of a patient in a bed between a plurality of separate positions of lying in the bed, comprising:
   a substrate for supporting elements to be displayed;
   a plurality of first display elements each providing an indication of a required position for the patient;
   the substrate providing a plurality of locations each for receiving a respective one of the first display elements;
   a second display element arranged to provide a display associated with a respective one of the locations for indicating a current position of the patient;
   a third display element arranged to provide a display indicating a next required position of the patient;

a fourth display element arranged to provide a display indicating a time for next movement of the patient to the next position.

2. The display apparatus according to claim 1 wherein there is provided an input for entering an indication of a maximum allowable time for the patient to remain in each position.

3. The display apparatus according to claim 2 wherein the fourth display element is arranged to display the time for next movement based on a calculation of adding the maximum allowable time to the current time.

4. The display apparatus according to claim 2 wherein there is provided control unit which receives the input of the maximum allowable time and automatically adds this to a clock signal indicating the current time.

5. The display apparatus according to claim 1 wherein the fourth display element is arranged to display the actual time for the next movement and a time period to elapse before the next movement.

6. The display apparatus according to claim 1 wherein there are six locations.

7. The display apparatus according to claim 1 wherein the locations are arranged sequentially around a center of the substrate.

8. The display apparatus according to claim 7 wherein the fourth display element is located in the center of the locations.

9. The display apparatus according to claim 1 wherein the first display elements each include a graphic symbol indicative of the respective position of the patient.

10. The display apparatus according to claim 1 wherein the fourth display comprises a graphic symbol of a clock.

11. The display apparatus according to claim 10 wherein the fourth display is set manually.

12. The display apparatus according to claim 1 wherein there is provided a further display element which indicates the requirement of the patient to be removed from the bed for meals.

13. The display apparatus according to claim 1 wherein there is provided a further display element which indicates the requirement of the patient to be removed from the bed for placement in a chair.

14. The display apparatus according to claim 1 wherein the substrate is arranged for removably receiving the first display elements for selective positioning in the locations.

15. The display apparatus according to claim 1 wherein the substrate is a magnetic board with a surface which can be marked and erased and wherein the first display elements are magnetic for selective positioning in the locations.

16. The display apparatus according to claim 15 wherein the second display element is arranged to be moved manually to a selected one of the locations.

17. The display apparatus according to claim 1 wherein the second display element comprises a plurality of illuminated buttons each associated with a respective location and each operable to indicate a selected one of the locations.

18. A method for managing movement of a patient in a bed between a plurality of separate positions of lying in the bed, comprising:
 providing a plurality of first display elements each providing an indication of a required position for the patient;
 causing a health care provider to enter an indication of a current position of the patient;
 providing a display indicating a next required position of the patient;
 entering an indication of a maximum allowable time for the patient to remain in each position;
 and providing a display indicating a time for next movement of the patient to the next position.

19. The method according to claim 18 wherein the time for next movement is based on a calculation of adding the maximum allowable time to the current time.

20. The method according to claim 18 wherein there is provided control unit which receives the input of the maximum allowable time and automatically adds this to a clock signal indicating the current time.

* * * * *